(12) United States Patent
Bal et al.

(10) Patent No.: US 9,174,200 B2
(45) Date of Patent: Nov. 3, 2015

(54) PROCESS FOR PREPARATION OF AG—W OXIDE CATALYST FOR THE SELECTIVE CONVERSION OF PROPYLENE TO PROPYLENE OXIDE WITH MOLECULAR OXYGEN

(71) Applicant: Council of Scientific and Industrial Research, New Delhi (IN)

(72) Inventors: Rajaram Bal, Mohkampur (IN); Shilpi Ghosh, Mohkampur (IN); Shubhra Acharyya Shanka, Mohkampur (IN); Bipul Sarkar, Mohkampur (IN); Chandrashekar Pendem, Mohkampur (IN); Rajib Kumar Singha, Mohkampur (IN)

(73) Assignee: Council of Scientific and Industrial Research (IN)

( * ) Notice: Subject to any disclaimer, the term of this patent is extended or adjusted under 35 U.S.C. 154(b) by 0 days.

(21) Appl. No.: 14/366,244

(22) PCT Filed: Dec. 21, 2012

(86) PCT No.: PCT/IN2012/000836
§ 371 (c)(1),
(2) Date: Jun. 17, 2014

(87) PCT Pub. No.: WO2013/098855
PCT Pub. Date: Jul. 4, 2013

(65) Prior Publication Data
US 2014/0364636 A1 Dec. 11, 2014

(30) Foreign Application Priority Data
Dec. 27, 2011 (IN) .......................... 3824/DEL/2011

(51) Int. Cl.
C07D 301/10 (2006.01)
B01J 23/00 (2006.01)
(Continued)

(52) U.S. Cl.
CPC ............ B01J 23/687 (2013.01); B01J 35/0013 (2013.01); B01J 35/06 (2013.01); B01J 37/036 (2013.01); B01J 37/16 (2013.01); C07D 301/10 (2013.01)

(58) Field of Classification Search
CPC ...... B01J 35/0013; B01J 35/06; B01J 37/036; B01J 37/16; B01J 23/687
USPC ........................ 549/534; 502/317; 423/594.13
See application file for complete search history.

(56) References Cited

FOREIGN PATENT DOCUMENTS
WO WO-98/52931 A1 11/1998
WO WO-2013/098855 7/2013

OTHER PUBLICATIONS

"International Application No. PCT/IN2012/000836, International Preliminary Report on Patentability dated Jul. 1, 2014", 5 pgs.
(Continued)

*Primary Examiner* — T. Victor Oh
(74) *Attorney, Agent, or Firm* — Schwegman Lundberg & Woessner, P.A.

(57) ABSTRACT

The present invention provides a process for preparation of Ag—W oxide catalyst for the direct and selective conversion of propylene to propylene oxide. The process provides a direct single step selective vapor phase oxidation of propylene to propylene oxide using molecular oxygen over Ag—W oxide catalysts. The process provides propylene conversion of 10-50% and selectivity for propylene oxide up to 100%.

10 Claims, 5 Drawing Sheets

Powder X-Ray Diffraction (XRD)

(51) Int. Cl.
*B01J 23/68* (2006.01)
*B01J 37/03* (2006.01)
*B01J 37/16* (2006.01)
*B01J 35/00* (2006.01)
*B01J 35/06* (2006.01)

(56) References Cited

OTHER PUBLICATIONS

"International Application No. PCT/IN2012/000836, International Search Report mailed Jun. 20, 2013", 4 pgs.

"International Application No. PCT/IN2012/000836, Written Opinion mailed Jun. 20, 2013", 4 pgs.

Chowdhury, Biswajit, et al., "Trimethylamine as a Gas-Phase Promoter: Highly Efficient Epoxidation of Propylene over Supported Gold Catalysts", *Angew. Chem. Int. Ed*, 45, (2006), 412-415.

Lu, Jiqing, et al., "Epoxidation of Propylene on NaCl-Modified $VCe_{1-x}Cu_x$ Oxide Catalysts with Direct Molecular Oxygen as the Oxident", *Journal of Catalysts*, 211, (2002), 552-555.

Lu, Jiqing, et al., "In situ UV—vis studies of the effect of particle size on the epoxidation of ethylene and propylene on supported silver catalysts with molecular oxygen", *Journal of Catalysts*, 232, (2005), 85-95.

Nijhuis, T. Alexander, et al., "Mechanistic Study into the Direct Epoxidation of Propene over Gold/Titania Catalysts", *J. Phys. Chem. B*, 109, (2005), 19309-19319.

Sheldon, R. A., "Catalysis and pollution prevention", *Chemistry & Industry*, [online], Retrieved from the Internet: <URL: http://www.highbeam.com/doc/1G1-19648721.html>, (Jan. 6, 1997), 2 pgs.

Sinha, Anil K., et al., "A Three-Dimensional Mesoporous Titanosilicate Support for Gold Nanoparticles: Vapor-Phase Epoxidation of Propene with High Conversion", *Angew. Chem. Int. Ed.*, 43, (2004), 1546-1548.

Sun, Shibin, et al., "$W18O49$ nanorods decorated with Ag/AgCl nanoparticles as highly-sensitive gas-sensing material and visible-light-driven photocatalyst", *Journal of Solid State Chemistry*, 184(8), (2011), 2190-2195.

Thommes, Thomas, et al., "Catalytic Vapor Phase Epoxidation of Propene with Nitrous Oxide as an Oxidant: Investigations on Catalyst Composition and Reaction Conditions", *Ind. Eng. Chem. Res.*, 49, (2010), 2624-2637.

Wang, Peng et al., "Ag/AgBr/$WO_3$ • H2O: Visible-Light Photocatalyst for Bacteria Destruction", *Inorganic Chemistry*, 48(22), (2009), 10697-10702.

Yao, Wei, et al., "Epoxidation of Propylene by Molecular Oxygen Over the $Ag-Y_2O_3-K_2O/\alpha-Al_2O_3$ Catalyst", *Catal Lett*, 119, (2007), 185-190.

Zhu, Wenming, et al., "Cu(I)-Catalyzed Epoxidation of Propylene by Molecular Oxygen", *J. Phys. Chem. C. 112*, (2008), 7731-7734.

Zuwei, Xi, et al., "Reaction-Controlled Phase-Transfer Catalysis for Propylene Epoxidation to Propylene Oxide", *Science*, 292, (2001), 1139-1141.

Huang, Jiahui, et al., "Propene Epoxidation with Dioxygen Catalyzed by Gold Clusters", *Angew. Chem. Int. Ed.*, 48, (2009), 7862-7866.

Powder X- Ray Diffraction (XRD)

Scanning Electron Microscopy (SEM)

Transmission Electron Microscopy (TEM)

XRD

SEM

TEM

PROCESS FOR PREPARATION OF AG—W OXIDE CATALYST FOR THE SELECTIVE CONVERSION OF PROPYLENE TO PROPYLENE OXIDE WITH MOLECULAR OXYGEN

PRIORITY CLAIM TO RELATED APPLICATIONS

This application is a U.S. national stage application filed under 35 U.S.C. §371 from International Application Serial No. PCT/IN2012/000836, which was filed Dec. 21, 2012, and published as WO 2013/098855 on Jul. 4, 2013, and which claims priority to Indian Application No. 3824/DEL/2011, filed Dec. 27, 2011, which applications and publication are incorporated by reference as if reproduced herein and made a part hereof in their entirety, and the benefit of priority of each of which is claimed herein.

FIELD OF THE INVENTION

The present invention relates to a process for preparation of $Ag_2O$—$WO_3$ catalyst for the selective conversion of propylene to propylene oxide with molecular oxygen. More particularly, the present invention relates to a process for the selective oxidation of propylene to propylene oxide with molecular oxygen over Ag—W oxide catalyst. More particularly, the present invention relates to a process for the vapour phase selective oxidation of propylene to propylene oxide by using molecular oxygen over Ag—W oxide catalyst.

BACKGROUND OF THE INVENTION

Propylene oxide (PO) is a versatile chemical intermediate used in a wide range of industrial and commercial products including polyether polyols, propylene glycols and propylene glycol ethers. By volume, it is among the top 50 chemicals produced in the world with the annual production of about 5 million tons. Industrial production of propylene oxide is mainly from co-oxidation of propylene with other chemicals but these technologies create additional side products. The major conventional manufacturing methods of PO are the chlorohydrins•process and the Halcon process. The chlohydrin process is being phased out because of environmental pollution, while the latter has the by product limitation. So a new technology with environmentally benign has to be developed for the production of propylene oxide. The main concern in the fine chemical and drug intermediates are the amount of waste generated per unit weight of desired product (called E-factor by R A Sheldon in Chemsitry & Industry, 6 Jan. 1997, P 13) and poor atom efficiencies (kg of product produced per Kg of reactants used) due to the use of stoichiometric reagents and minerals acid/base catalysts. In this context, the use of solid catalysts which are eco-safe and reusuable become important. Moreover a major problem with this process is that it produces phenol is driving its price down and also hurting the economics of phenol as well. This concern is the impetus for researchers to develop a direct single step co-product free and environment friendly route to propylene oxide.

There are reports on the production of propylene oxide by direct oxidation of propylene with different oxidants over different solid catalyst but to the best of our knowledge there is no reference for the use of molecular oxygen only for this purpose.

Reference may be made to article in the Science 2001, 292, 1139-1141 by Chinese group Zuwei et al the use of $H_2O_2$ as the oxidizing agent for the conversion of propylene oxide from propylene to achieve ~85% yield over W containing heteropolyacid.

Reference may be made to article in the Journal of Catalysis 2002, 211, 552-555 by Can Li and his group reported the use of mixture of $H_2$ and $O_2$ for the oxidation of propylene to propylene oxide to achieve ~1% conversion and 43% propylene oxide selectivity over NaCl-modified $VCe_{1-x}Cu_x$ oxide catalyst.

Reference may be made to article in the Journal of Phys. Chem. B., 2005, 109, 19309-19319 by Nijhuis et al reported the use of $H_2+O_2$ as oxidants for the conversion of propylene to propylene oxide with ~4% propylene conversion and 95% propylene oxide selectivity over Au supported titania catalyst.

Reference may be made to article in the Journal of Catalysis, 2005, 232, 85-95, in which Oyama et al and his group reported the use of molecular oxygen for the oxidation of propylene to propylene oxide to achieve ~30 propylene conversion with ~10% propylene oxide selectivity over Ag supported $CaCO_3$ catalyst.

Reference may be made to article in the Angew. Chem. Int. Ed. 2004, 43, 1546-1548, in which Japanese worker Prof Haruta and his group reported the use of mixture of $H_2+O_2$ for the oxidation of propylene to propylene oxide to achieve 10% conversion and ~90% selectivity over $Ba(NO_3)_2$-Au/titanosilicate catalyst.

Reference may also be made to article in the Angew. Chem. Int. Ed. 2006, 45 412-415, in which the same Japanese worker Prof Haruta and his group reported the use of mixture of $H_2+O_2$ for the oxidation of propylene to propylene oxide to achieve 9% conversion and ~90% selectivity over gold supported titanosilicate catalyst, where small amount of trimethyl amine was introduced with the feed mixture.

Reference may be made to article in the Catalysis Lett. 2007, 119, 185-190 in which Lu et al reported the use of molecular oxygen as the oxidizing agent for the oxidation of propylene to propylene oxide to achieve 4% propylene conversion and 46.8% propylene oxide selectivity over Ag—$Y_2O_3$—$K_2O/Al_2O_3$ catalyst.

Reference may also be made to article in the Journal of Phys. Chem. C, 2008, 112, 7731-7734 in which Wang et al reported the use of molecular oxygen as the oxidizing agent to convert propylene to propylene oxide with a propylene conversion of ~4% with a propylene oxide selectivity of 55% over $CuO_x$—$SiO_2$ catalyst.

Reference may also be made to article in the Ind. Eng. Chem. Res. 2010, 49, 2614-2637 in which Bettina et al reported the use of nitrous oxide as the oxidizing agent for the oxidation of propylene to propylene oxide to achieve ~10% conversion and ~75% propylene oxide selectivity over $Fe/SiO_2$ catalyst.

Reference may also be made to article in the Angew. Chem. Int. Ed. 2009, 48 1546-1548, in which the same Japanese worker Prof Haruta and his group reported the use of mixture of $H_2O+O_2$ for the oxidation of propylene to propylene oxide to achieve 0.8% conversion and ~57% selectivity over gold supported TS-1 catalyst.

The drawback of the processes reported so far is that they do not exhibit sufficiently high conversions of propylene for high selectivity of propylene oxide to be of interest for industrial application. In most of the cases hazardous oxidizing agent $N_2O$, $H_2O_2$ or expensive $H_2$ with $O_2$ was used and also lots of unnecessary by-products was formed. In addition, the catalysts used have a limited activity under the operating conditions. There is, therefore, an evident necessity for further improvements in the process for the selective conversion of propylene to propylene oxide.

OBJECTS OF THE INVENTION

The main object of the present invention is to provide a process for preparation of Ag—W oxide catalyst for the selective conversion of propylene to propylene oxide with molecular oxygen.

Another objective of the present invention is to provide a process for the vapour phase selective oxidation of propylene to propylene oxide using oxygen as the oxidant and Ag—W-oxide as the catalyst.

Still another object of the present invention is to provide a process to obtain propylene oxide from propylene with high selectivity.

Yet another object of the present invention is to provide a process which uses environmental friendly green oxidizing agent, oxygen for the synthesis of propylene oxide.

Still another object of the present invention is to provide a process which works under continuous process for the synthesis of propylene oxide.

Yet another object of the present invention is to provide a catalyst with the mixture of Ag and W oxide which can be prepared easily and also very economical to produce propylene oxide from propylene.

SUMMARY OF THE INVENTION

Accordingly, the present invention provides a process for the preparation of Ag—W oxide catalyst, wherein the said process comprising the steps of;
a. mixing a salt of Ag preferably, $AgNO_3$, $WO_3.2H_2O$, a surfactant preferably, cetyltrimethylammonium bromide (CTAB), a reducing agent, preferably, hydrazine, $H_2O$ to obtain a gel;
b. mixing gel as obtained in step (a) with constant stirring for 2-6 h at room temperature ranging between 25-35° C.;
c. filtering the gel as obtained in step (b) and washing with excess water and dried in an oven with temperature range of 100-120° C. for a period ranging between 6-18 h.
d. calcining the dried product as obtained in step (c) at temperature range of 300-750° C. for a period ranging between 4-10 h to obtain Ag—W oxide catalyst.

In an embodiment of the invention, weight ratio of Ag to W in step (a) is in the range of 0.03 to 0.5.

In one embodiment of the invention, molar ratio of Ag to CTAB in step (a) is in the range of 0.75-1.3.

In another embodiment of the invention, molar ratio of Ag to hydrazine in step (a) is in the range of 0.75-1.3.

In yet another embodiment, a process for selective oxidation (epoxidation) of propylene to propylene oxide using Ag—W oxide catalyst, wherein the said process comprising the steps of reacting propylene with oxygen in the presence of Ag—W-oxide catalyst in the pressure range of 1-5 Mpa, at a temperature ranging between 150-450° C. with a weight hourly space velocity (WHSV, feed/g catalyst/hour) in the range of 2000 to 30000 $h^{-1}$ for a period in the range of 1-20 hours to obtain propylene oxide.

In still another embodiment, the conversion of propylene oxide is in the range of 10-50%.

In still another embodiment, selectivity of the propylene oxide obtained in the range of 80-100%.

In still another embodiment, the yield of propylene oxide is in the range of 10-50%.

In still another embodiment, Ag—W oxide catalyst having molecular formula $Ag_2O$—$WO_3$ which comprises of 2-20 wt % Ag and 60-85% wt % W in wt % and oxygen 5-30 wt %

There were four diffraction peaks of Ag at 2θ=38.1, 44.3, 64.4 and 77.4° corresponding to the crystal faces of Ag(111), (200), (220) and (311), respectively, which coincide well with the literature values (JCPDS No. 04-0783).

Figure 1:
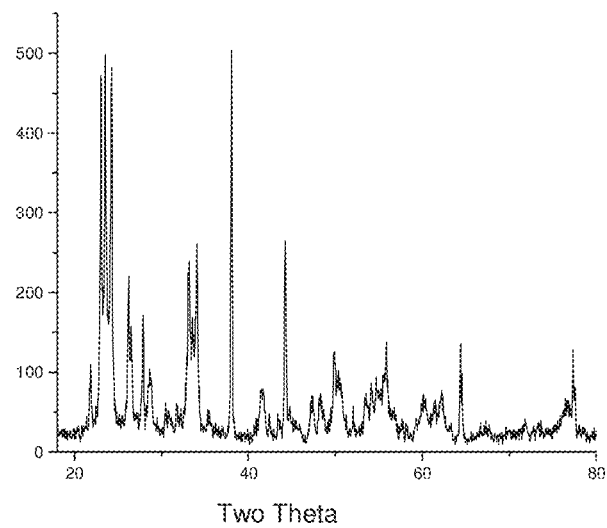
FIG. 1 shows the main peaks at 23.22, 24.5, 23.72 and 34.25° (2θ) are due to the WO3 support (example 1).
Figure 2:
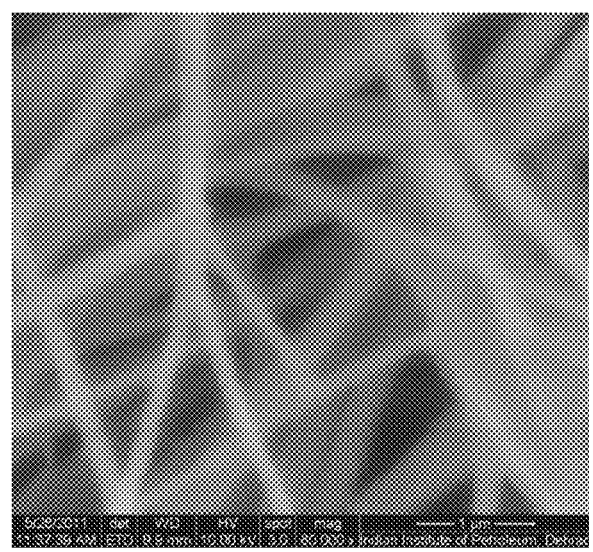

FIG. 2 Low magnification SEM image image shows that uniform rod-like structure with diameter around 30-40 nm and length upto several microns(example 1).

Figure 3:
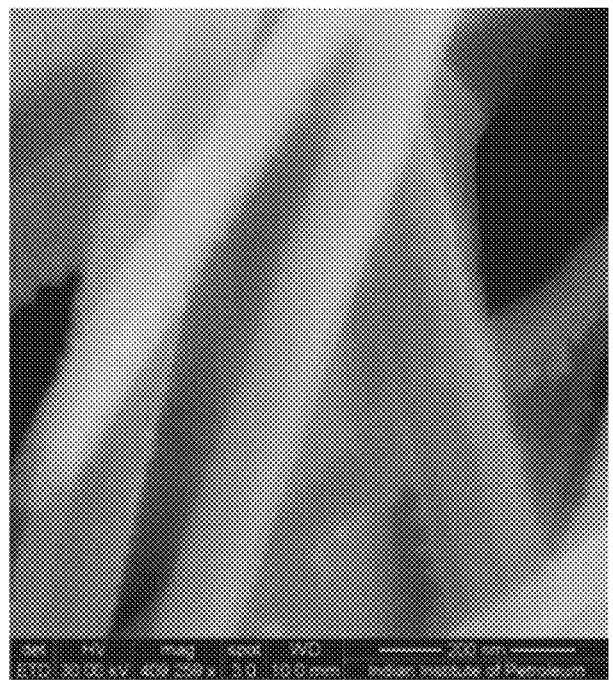

FIG. 3 High magnification SEM image shows that Ag nanoparticles supported on uniform rod-like structure with diameter around 30-40 nm and length upto several microns attending a high aspect ratio (example 1).

Figure 4:
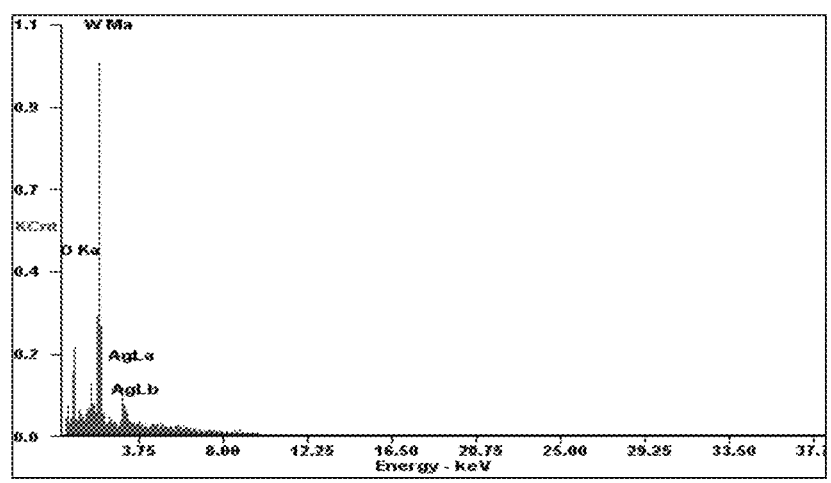

FIG. 4 Energy Dispersive X-ray analysis (EDAX) analysis showing the presence of Ag, W, O in the catalyst (example 1).

Figure 5:
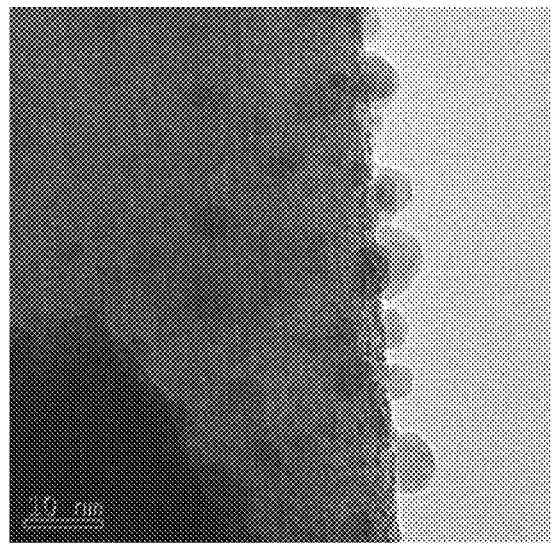
Figure 5:
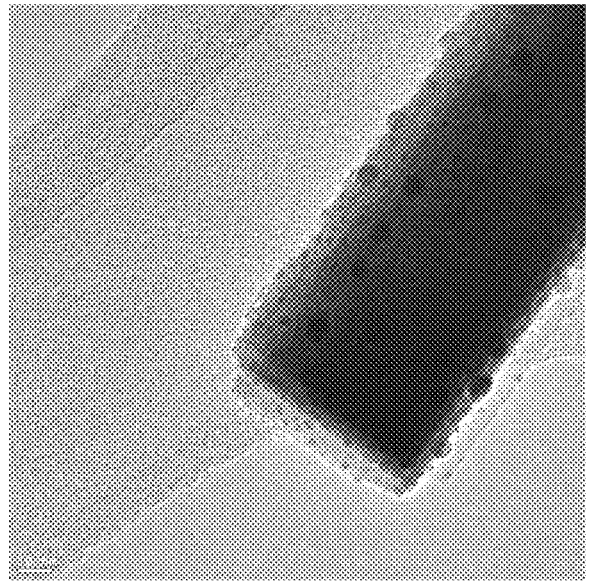

FIG. 5 High resolution tranmission electron microscopy (HRTEM) revealed a rod-like morphology of tungsten oxide with an average width of 30 nm covered by ordered silver particles with size nearly 5 nm (example 1).

Figure 6:
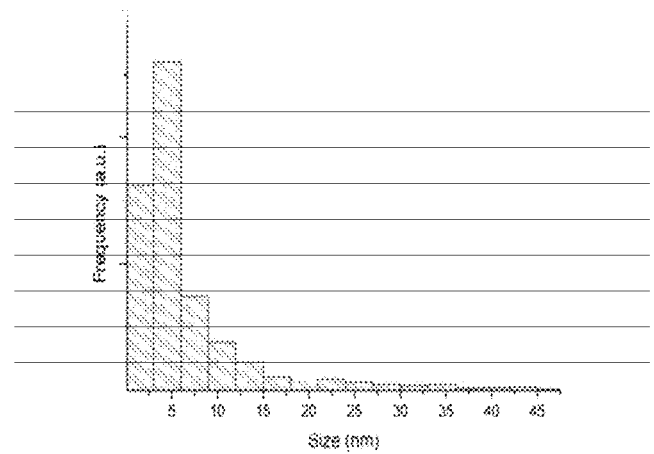

FIG. 6 Size distribution of silver nanoparticles (example 1).

Figure 7:
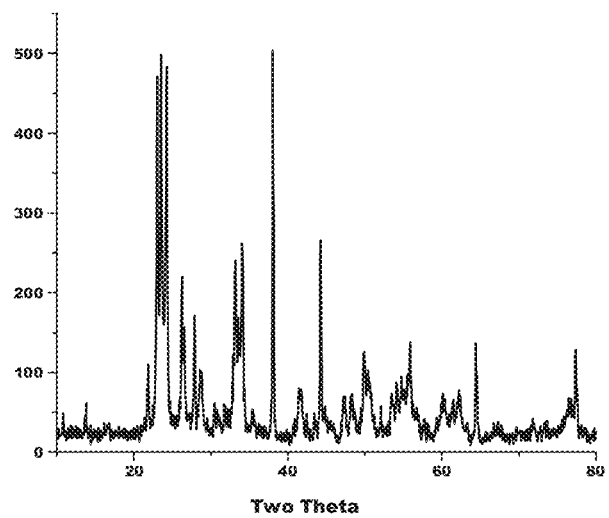
Figure 8:
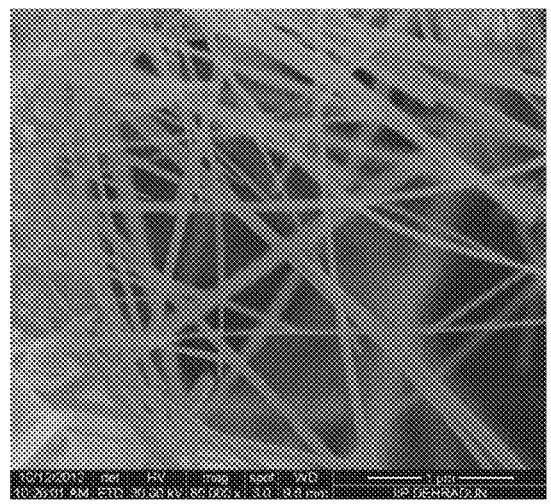
Figure 9:

FIG. 7 shows the XRD of catalyst prepared in example 2
FIG. 8 shows the SEM of catalyst prepared in example 2
FIG. 9 shows the TEM of catalyst prepared in example 2

DETAILED DESCRIPTION OF THE INVENTION

The present invention provides a process for the preparation of Ag—W-oxide (Ag nanoparticles supported on WO3 nanorod) catalyst by room temperature synthesis for the preparation of propylene oxide by vapour phase selective epoxidation of propylene using oxygen as the oxidant involves the following steps The process for the preparation of Ag—W-oxide catalyst comprising the steps of preparation of the gel composition using $AgNO_3$, $WO_3.2H_2O$, cetyltrimethylammonium bromide, hydrazine, $H_2O$ where $AgNO_3$, $WO_3.2H_2O$ are the precursors for Ag and W respectively.

The weight ratio of Ag to W was varied in the range between 0.03 to 0.5

The molar ratio of Ag to CTAB varied in the range of 0.75-1.3

The molar ratio of Ag to hydrazine varied in the range of 0.75-1.3

The mixing gel was stirred for 2-6 h at room temperature
The product was filterer with excess water and dried in an oven with temperature range of 100-120° C. The dried product was calcined in a furnace in the temperature range of 300-750° C.

General Procedure for the Conversion of Propylene to Propylene Oxide

The reaction was carried out in a fixed bed down flow high pressure reactor by charging a catalyst for 1 to 30 h to get propylene oxide. The pressure of the reactor was maintained by using oxygen and the oxygen pressure is preferably in the range 2 to 5 MPa. The reaction temperature is preferably in the range 150-400° C. The weight hourly space velocity (WHSV) is preferably in the range 5000 to 20000 ml/hr/gm. Propylene was introduced in the reactor by using mass flow controller. The reaction mixtures were analysed by two online GCs with an FID detector by using capillary column for hydrocarbons and a TCD detector by using a Porapack-Q column for inorganic materials.

The following examples are given by way of illustration of the working of the invention in actual practice and should not be construed to limit the scope of the present invention in any way.

Example 1

An aqueous solution of a given amount of silver nitrate (AgNO3, 0.787 g) was added to vigorously stirred tungstic acid (H2WO4, 10.77 g) solution. The pH of the medium was made 9 by adding ammonium hydroxide solution. Then an aqueous solution of cetyltrimethyl ammonium bromide (CTAB, 1.26 g) was added to the mixture of two metal precursors. Finally, 0.28 g of aqueous solution of hydrazine was added drop wise. The reagents were added maintaining the following molar ratio:

Ag:CTAB:$H_2O$:hydrazine=1:0.75:300:1.

After stirring 4 hrs at room temperature (25° C.) until a homogeneous solution was obtained, the resultant mixed species was washed with ethanol, and dried at 110° C., for 24 hours, followed by calcination at 650° C. for 5 hrs.

The catalyst can be denoted as $Ag_2O$—$WO_3$ (5 wt % Ag, 75.4% W and 19.6 wt % O Example 2

An aqueous solution of a given amount of silver nitrate (AgNO3, 1.574 g) was added to vigorously stirred tungstic acid (H2WO4, 10.77 g) solution. The pH of the medium was made 9 by adding ammonium hydroxide solution. Then an aqueous solution of cetyltrimethyl ammonium bromide (CTAB, 1.26 gm) was added to the mixture of two metal precursors. Lastly, 0.28 gm of aqueous solution of hydrazine was added drop wise. The reagents were added maintaining the the following molar ratio:

Ag:CTAB:H2O:hydrazine=1:0.75:300:1.

After stirring 4 hrs at room temperature (25° C.) until a homogeneous solution was obtained, the resultant mixed species was washed with ethanol, and dried at 130° C., for 24 hours, followed by calcination at 700° C. for 4 hrs.

The catalyst can be denoted as $Ag_2O$—$WO_3$ (10 wt % Ag, 71.3% W and 18.7 wt % O).

Example 3

This example describes the epoxidation of propylene to propylene oxide by vapour phase reaction in presence of oxygen using Ag supported W-oxide as the catalyst.

Process Conditions

Catalyst: Silver supported on tungsten oxide nanorod 0.3 g (catalyst prepared in Example 1 was used)
Ag:W oxide weight ratio in the catalyst=1:20
Oxygen pressure: 3 Mpa
Weight hourly space velocity (WHSV): 10000 $h^{-1}$
Temperature: 375° C.
Reaction time: 6 h
Product analysis:
Propylene conversion: 45%
Selectivity of propylene oxide: 100%
Yield of propylene: 45%

Example 4

The example describes the effect of temperature on yield and selectivity of propylene oxide. The product analysis presented in Table—1.

Process Conditions:
Catalyst: Silver supported on tungsten oxide nanorod 0.3 g (catalyst prepared in Example 1 was used)
Ag:W-oxide weight ratio in the catalyst=1:20
Oxygen pressure: 3 Mpa
Weight hourly space velocity (WHSV): 10000 $h^{-1}$
Reaction time: 6 h

TABLE 1

Effect of temperature on propylene conversion, propylene oxide yield and selectivity

| Temperature (° C.) | Propylene Conversion (%) | Propylene oxide Yield | Selectivity |
|---|---|---|---|
| 200 | 15.8 | 15.8 | 100 |
| 250 | 20.3 | 20.3 | 100 |
| 300 | 24.6 | 24.6 | 100 |
| 350 | 36.3 | 36.3 | 100 |
| 400 | 48.7 | 47.3 | 97.1 |

Example 5

The example describes the effect of time on stream on yield and selectivity of propylene oxide. The product analysis presented in Table 2

Process Conditions:
Catalyst: 0.3 g (catalyst prepared in Example 1 was used)
Ag:W-oxide weight ratio in the catalyst=1:20
Oxygen pressure: 3 Mpa
Weight hourly space velocity (WHSV): 10000 $h^{-1}$
Reaction temperature: 375° C.

TABLE 2

Effect of time on stream on propylene conversion, propylene oxide yield and selectivity

| Time on stream (h) | Propylene Conversion (%) | Propylene oxide Yield | Selectivity |
|---|---|---|---|
| 2 | 44.8 | 44.8 | 100 |
| 6 | 45.0 | 45.0 | 100 |
| 12 | 45.1 | 45.1 | 100 |
| 18 | 45.4 | 45.4 | 100 |
| 28 | 44.9 | 44.9 | 100 |

Example 6

The example describes the effect of oxygen pressure on yield and selectivity of propylene oxide. The product analysis presented in Table—3.

Process Conditions:
Catalyst: Silver supported on tungsten oxide nanorod 0.3 g (catalyst prepared in Example 1 was used)
Ag:W-oxide weight ratio in the catalyst=1:20
Weight hourly space velocity (WHSV): 10000 $h^{-1}$
Temperature: 375° C.
Reaction time: 6 h

TABLE 3

Effect of oxygen pressure on propylene conversion, propylene oxide yield and selectivity

| Reaction Pressure (MPa) | Propylene Conversion (%) | Propylene oxide Yield | Propylene oxide Selectivity |
|---|---|---|---|
| 2 | 17.3 | 17.3 | 100 |
| 3 | 45.0 | 45 | 100 |
| 4 | 46.1 | 43.8 | 95.1 |
| 5 | 47.3 | 39.9 | 84.3 |

Example 7

The example describes the effect of weight hourly space velocity on yield and selectivity of propylene oxide. The product analysis presented in Table—4.

Process Conditions:
Catalyst: Silver supported on tungsten oxide nanorod 0.3 g (catalyst prepared in Example 1 was used)
Ag:W-oxide weight ratio in the catalyst=1:20
Oxygen pressure: 3 Mpa
Temperature: 375° C. Reaction time: 6 h

TABLE 4

Effect of weight hourly space velocity (WHSV) on propylene conversion, propylene oxide yield and selectivity

| WHSV (ml feed/h/$g_{cat}$) | Propylene Conversion (%) | Propylene oxide Yield | Propylene oxide Selectivity |
|---|---|---|---|
| 3000 | 49.1 | 44.9 | 91.4 |
| 6000 | 46.6 | 44.8 | 96.2 |
| 10000 | 45.0 | 45 | 100 |
| 20000 | 35.1 | 35.1 | 100 |

The main advantages of the present invention are:
1. The process of the present invention converts propylene to propylene oxide in a single step with a single catalyst.
2. The process provides not only good conversion but also good selectivity for propylene oxide.
3. The oxidizing agent, oxygen, used in this process has the major advantages of this process.
4. The process does not produce any by-products is also a major advantage of this process.
5. The process does not need any additional reagent to generate active oxygen.
6. The catalyst is used in very low amounts.
7. The catalyst does not deactivate till 30 h with the reaction stream.

We claim:

1. A process for the preparation of Ag—W oxide catalyst, said process comprising the steps of:
   a. mixing a salt of Ag, $WO_3.2H_2O$, a surfactant, a reducing agent hydrazine and $H_2O$ to obtain a gel;
   b. mixing gel as obtained in step (a) with constant stirring for 2-6 h at room temperature ranging between 25-35° C.;
   c. filtering the gel as obtained in step (b) and washing with excess water and dried in an oven with temperature ranging between 100-120° C. for a period ranging between 6-18 hours; and
   d. calcining the dried product as obtained in step (c) at temperature ranging between 300-750° C. for a period ranging between 4-10 h to obtain Ag—W oxide catalyst.

2. The process as claimed in claim 1, wherein weight ratio of Ag to W in step (a) is in the range of 0.03 to 0.5.

3. The process as claimed in claim 1, wherein the surfactant is cetyltrimethylammonium bromide (CTAB) and the molar ratio of Ag to CTAB in step (a) is in the range of 0.75-1.3.

4. The process as claimed in claim 1, wherein molar ratio of Ag to hydrazine in step (a) is in the range of 0.75-1.3.

5. A single step process for selective oxidation (epoxidation) of propylene to propylene oxide using Ag—W oxide catalyst as obtained by the process as claimed in claim 1, wherein the said process comprising the steps of reacting propylene with oxygen in the presence of Ag—W— oxide catalyst in the pressure range of 1-5 Mpa, at a temperature ranging between 150-450° C. with a weight hourly space velocity (WHSV, feed/g catalyst/hour) in the range of 2000 to 30000 $h^{-1}$ for a period in the range of 1-20 hours to obtain propylene oxide.

6. The process as claimed in claim 5, wherein the conversion of propylene oxide is in the range of 10-50%.

7. The process as claimed in claim 5, wherein the selectivity of the propylene oxide obtained in the range of 80-100%.

8. The process as claimed in claim 5, wherein the yield of propylene oxide is in the range of 10-50%.

9. The process as claimed in claim 1, wherein the salt of Ag is $AgNO_3$.

10. The process as claimed in claim 1, wherein the surfactant is cetyltrimethylammonium bromide (CTAB).

* * * * *